(12) United States Patent
Rajan et al.

(10) Patent No.: US 12,708,779 B2
(45) Date of Patent: Aug. 18, 2026

(54) SYSTEMS AND METHODS FOR DETECTING ARRHYTHMIAS

(71) Applicant: Cardiac Pacemakers, Inc., St. Paul, MN (US)

(72) Inventors: Abhijit Rajan, Shoreview, MN (US); Deepa Mahajan, North Oaks, MN (US); David L. Perschbacher, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 720 days.

(21) Appl. No.: 18/073,215

(22) Filed: Dec. 1, 2022

(65) Prior Publication Data

US 2023/0173282 A1 Jun. 8, 2023

Related U.S. Application Data

(60) Provisional application No. 63/286,386, filed on Dec. 6, 2021.

(51) Int. Cl.
*A61N 1/365* (2006.01)
*A61N 1/02* (2006.01)

(52) U.S. Cl.
CPC ......... *A61N 1/36585* (2013.01); *A61N 1/025* (2013.01)

(58) Field of Classification Search
CPC ...... A61B 5/361; A61B 5/363; A61N 1/3621; A61N 1/3624; A61N 1/395
See application file for complete search history.

(56) References Cited

U.S. PATENT DOCUMENTS

| | | | |
|---|---|---|---|
| 10,702,180 | B2 | 7/2020 | Perschbacher et al. |
| 10,744,334 | B2 | 8/2020 | Perschbacher et al. |
| 11,051,746 | B2 | 7/2021 | Krueger et al. |

(Continued)

FOREIGN PATENT DOCUMENTS

| | | | |
|---|---|---|---|
| CN | 118541193 | A | 8/2024 |
| EP | 2086402 | | 8/2009 |
| WO | WO-2023107330 | A1 | 6/2023 |

OTHER PUBLICATIONS

"International Application Serial No. PCT US2022 051520, International Search Report mailed Mar. 13, 2023", 5 pages.

(Continued)

*Primary Examiner* — George R Evanisko
(74) *Attorney, Agent, or Firm* — Nelson Mullins Riley & Scarborough LLP

(57) ABSTRACT

Systems and methods for detecting cardiac arrhythmias such as atrial tachyarrhythmia (AT) are discussed. An exemplary system includes an arrhythmia detector circuit that can receive physiologic information sensed from a patient over time, detect an arrhythmia onset when the physiologic information during a first time period satisfies an onset condition, and in response to the detected arrhythmia onset, detect an arrhythmia termination when the physiologic information during a second time period, subsequent to and longer than the first time period, satisfies an exit condition. An arrhythmia episode can be detected based on an arrhythmia duration between the detected onset and termination. The detected sustained arrhythmia episode can be provided to a user or a processor for further processing.

20 Claims, 6 Drawing Sheets

(56) References Cited

U.S. PATENT DOCUMENTS

| | | | | |
|---|---|---|---|---|
| 2008/0188764 | A1* | 8/2008 | Lee | A61N 1/3925 600/509 |
| 2008/0300497 | A1 | 12/2008 | Krause et al. | |
| 2017/0319862 | A1 | 11/2017 | Foshee, Jr. et al. | |
| 2019/0231207 | A1 | 8/2019 | Perschbacher et al. | |
| 2020/0093388 | A1* | 3/2020 | Bouguerra | A61B 5/361 |
| 2020/0178826 | A1 | 6/2020 | Mahajan et al. | |
| 2020/0269055 | A1 | 8/2020 | Kleckner et al. | |

OTHER PUBLICATIONS

"International Application Serial No. PCT US2022 051520, Written Opinion mailed Mar. 13, 2023", 5 pages.

"European Application Serial No. 22843550.9, Response to Communication Pursuant to Rules 161 and 162 filed Jan. 16, 2025", 12 pgs.

"International Application Serial No. PCT/US2022/051520, International Preliminary Report on Patentability mailed Jun. 20, 2024", 7 pgs.

* cited by examiner

SYSTEMS AND METHODS FOR DETECTING ARRHYTHMIAS

CLAIM OF PRIORITY

This application claims the benefit of U.S. Provisional Application No. 63/286,386, filed on Dec. 6, 2021, which is hereby incorporated by reference in its entirety.

TECHNICAL FIELD

This document relates generally to medical devices, and more particularly, to systems, devices and methods for detecting and managing cardiac arrhythmias.

BACKGROUND

Implantable medical devices (IMDs) have been used for monitoring patient health condition or disease states and delivering therapies. For example, implantable cardioverter-defibrillators (ICDs) may be used to monitor for certain abnormal heart rhythms and to deliver electrical energy to the heart to correct the abnormal rhythms. Some IMDs may be used to monitor for chronic worsening of cardiac hemodynamic performance, such as due to congestive heart failure (CHF), and to provide cardiac stimulation therapies, including cardiac resynchronization therapy (CRT) to correct cardiac dyssynchrony within a ventricle or between ventricles.

Some IMDs can detect cardiac arrhythmias, such as atrial tachyarrhythmia (AT). One type of AT event is atrial fibrillation (AF), recognized as the most common clinical arrhythmia affecting millions of people. During AF, disorganized electrical pulses originated from regions in or near an atrium may lead to irregular conductions to ventricles, thereby causing inappropriately fast and irregular heart rate. AF may be paroxysmal that may last from minutes to days before it stops by itself. Persistent AF may last for over a week and typically requires medication or other treatment to revert to normal sinus rhythm. AF is permanent if a normal heart rhythm cannot be restored with treatment. AF may be associated with stroke and requires anticoagulation therapy.

Another type of AT event is atrial flutter (AFL). AFL usually accompanies with some degree of atrioventricular (AV) node conduction block, and can be associated with a fast and usually regular heart rate. Typical or Type I AFL may involve a single reentrant circuit in the right atrium around the tricuspid valve annulus, and has an atrial rate of 240 to 340 beats per minute (bpm). The reentrant circuit most often travels in a counter-clockwise direction. Atypical or Type II AFL follows a different circuit, which may involve the right or the left atrium, and usually has a faster atrial rate of around 340-440 bpm. AFL may be associated with a variety of cardiac disorders, such as coronary artery disease (CAD) or hypertensive heart disease. AFL may often degenerate into AF. Prolonged fast AFL may lead to decompensation with loss of normal heart function. This may manifest as effort intolerance, nocturnal breathlessness, or swelling of the legs or abdomen.

Some IMDs can detect cardiac arrhythmia episode, such as an AT episode, by separately detecting an arrhythmia onset and an arrhythmia termination. The arrhythmia duration between the detected arrhythmia onset and the detected arrhythmia termination can be used to characterize the underlying arrhythmia, such as an AT burden which can be defined as total time or a proportion of time an individual is in AT rhythm during a specific monitoring period.

OVERVIEW

Timely detection of atrial tachyarrhythmia, such as AF or AFL, may be clinically important for assessing cardiac function. In some instances and/or in some patients, implantable or wearable cardiac devices may detect a large volume of superfluous "short" AT episodes characterized by short AT durations from onset to termination, and are separated in time by short time gaps. Superfluous AT episodes may be caused by the device being overly sensitive to noise or temporary stabilization of heart rate (i.e., reduced variability in heart rate) over a long and sustained underlying AT event, and can affect patient treatment, increase clinician workload as well as healthcare cost in patient management.

Embodiments of systems, devices, and methods discussed in this document can improve device-based cardiac arrhythmia detection and patient management, and in particular can avoid or reduce detections of superfluous short arrhythmia episodes which represent portions of a long and sustained underlying arrhythmia event. An exemplary system includes an arrhythmia detector circuit that can receive physiologic information sensed from a patient over time, detect an arrhythmia onset when the physiologic information during a first time period satisfies an onset condition, and in response to the detected arrhythmia onset, detect an arrhythmia termination when the physiologic information during a second time period, subsequent to and longer than the first time period, satisfies an exit condition. An arrhythmia episode can be detected based on an arrhythmia duration between the detected onset and termination. The detected sustained arrhythmia episode can be provided to a user or a processor for further processing.

Example 1 is a system for detecting cardiac arrhythmia in a patient, comprising: an arrhythmia detector circuit configured to: receive physiologic information sensed from a patient over time; detect an arrhythmia onset when the received physiologic information during a first time period satisfies an onset condition; in response to the detected arrhythmia onset, detect an arrhythmia termination when the received physiologic information during a second time period, subsequent to and longer than the first time period, satisfies an exit condition different than the onset condition; and detect an arrhythmia episode based on an arrhythmia duration between the detected arrhythmia onset and the detected arrhythmia termination; and an output unit configured to provide the detected arrhythmia episode to a user or a processor.

In Example 2, the subject matter of Example 1 optionally includes the first time period that can include a first time window, and the second time period that can include two consecutive time windows subsequent to the first time window, and the arrhythmia detector circuit that can be configured to detect the arrhythmia termination when respective physiologic information in each of the two consecutive time windows of the second time period separately satisfy the exit condition.

In Example 3, the subject matter of Example 2 optionally includes the two consecutive time windows each having a time duration substantially equal to a duration of the first time window.

In Example 4, the subject matter of any one or more of Examples 1-3 optionally includes the arrhythmia detector circuit that can be configured to detect the arrhythmia episode including an atrial tachyarrhythmia episode.

In Example 5, the subject matter of any one or more of Examples 2-4 optionally includes the onset condition that can include an initial criterion and a confirmation criterion, and the arrhythmia detector circuit that can be configured to detect the arrhythmia onset when the received physiologic information in the first time window satisfies both the initial detection criterion and the confirmation criterion.

In Example 6, the subject matter of Example 5 optionally includes the confirmation criterion that can have a higher specificity of detecting the cardiac arrhythmia than the initial detection criterion.

In Example 7, the subject matter of any one or more of Examples 5-6 optionally includes the arrhythmia detector circuit that can be configured to: generate a first signal metric and a different second signal metric from the received physiologic information in the first time window; and determine that the received physiologic information in the first time window satisfies the initial criterion using the first signal metric, and satisfies the confirmation criterion using the second signal metric.

In Example 8, the subject matter of Example 7 optionally includes the cardiac arrhythmia that can include atrial tachyarrhythmia, the first metric that can include at least one of an atrial heart rate or a ventricular heart rate variability, and the second metric that can include at least one of: a ventricular rate cluster; a Wenckebach score; a double-decrement ratio; or a cardiac signal morphology.

In Example 9, the subject matter of any one or more of Examples 2-8 optionally includes the exit condition that can include an initial criterion and a confirmation criterion for each of the two consecutive time windows, and the arrhythmia detector circuit that can be configured to detect the arrhythmia termination (i) when the respective physiologic information in at least one of the two consecutive time windows fails the initial criterion, or (ii) when the respective physiologic information in each of the two consecutive time windows separately fail the confirmation criterion.

In Example 10, the subject matter of Example 9 optionally includes the confirmation criterion that can have a higher specificity of detecting the cardiac arrhythmia than the initial detection criterion.

In Example 11, the subject matter of any one or more of Examples 9-10 optionally includes the arrhythmia detector circuit that can be configured to: generate a first signal metric and a different second signal metric from the respective physiologic information in each of the two consecutive time windows; and for each of the two consecutive time windows, determine that the respective physiologic information in the corresponding time window fails the initial criterion using the first signal metric, or fails the confirmation criterion using the second signal metric.

In Example 12, the subject matter of Example 11 optionally includes the cardiac arrhythmia that can include atrial tachyarrhythmia, the first metric that can include at least one of an atrial heart rate or a ventricular heart rate variability, and the second metric that can include at least one of: a ventricular rate cluster; a Wenckebach score; a double-decrement ratio; or a cardiac signal morphology.

In Example 13, the subject matter of any one or more of Examples 1-12 optionally includes the arrhythmia detector circuit that can be configured to detect the arrhythmia episode including a sustained arrhythmia episode if the arrhythmia duration exceeds a threshold, or a non-sustained arrhythmia episode if the arrhythmia duration is below the threshold.

In Example 14, the subject matter of any one or more of Examples 1-13 optionally includes an implantable cardiac monitor that includes the arrhythmia detector circuit.

In Example 15, the subject matter of any one or more of Examples 1-14 optionally includes a therapy unit configured to provide therapy to the patient in response to the detected arrhythmia episode.

Example 16 is a method for detecting cardiac arrhythmia in a patient, the method comprising: receiving physiologic information sensed from a patient over time; detecting, via an arrhythmia detector circuit, an arrhythmia onset when the received physiologic information during a first time period satisfies an onset condition; in response to the detected arrhythmia onset, detecting, via the arrhythmia detector circuit, an arrhythmia termination when the received physiologic information during a second time period, subsequent to and longer than the first time period, satisfies an exit condition different than the onset condition; detecting an arrhythmia episode based on an arrhythmia duration between the detected arrhythmia onset and the detected arrhythmia termination; and providing the detected arrhythmia episode to a user or a process.

In Example 17, the subject matter of Example 16 optionally includes the first time period that can include a first time window, and the second time period that can include two consecutive time windows subsequent to the first time window each having a time duration substantially equal to a duration of the first time window, and wherein detecting the arrhythmia termination occurs when respective physiologic information in each of the two consecutive time windows of the second time period separately satisfy the exit condition.

In Example 18, the subject matter of Example 17 optionally includes the onset condition that can include an initial criterion and a confirmation criterion, and wherein detecting the arrhythmia onset occurs when the received physiologic information in the first time window satisfies both the initial detection criterion and the confirmation criterion.

In Example 19, the subject matter of Example 18 optionally includes: generating a first signal metric and a different second signal metric from the received physiologic information in the first time window; and determining that the received physiologic information in the first time window satisfies the initial criterion using the first signal metric, and satisfies the confirmation criterion using the second signal metric.

In Example 20, the subject matter of any one or more of Examples 17-19 optionally includes the exit condition that can include an initial criterion and a confirmation criterion for each of the two consecutive time windows, and wherein detecting the arrhythmia termination occurs (i) when the respective physiologic information in at least one of the two consecutive time windows fails the initial criterion, or (ii) when the respective physiologic information in each of the two consecutive time windows fails the confirmation criterion.

In Example 21, the subject matter of Example 20 optionally includes: generating a first signal metric and a different second signal metric from the respective physiologic information in each of the two consecutive time windows; and for each of the two consecutive time windows, determining that the respective physiologic information in the corresponding time window fails the initial criterion using the first signal metric, or fails the confirmation criterion using the second signal metric.

In Example 22, the subject matter of any one or more of Examples 16-21 optionally includes detecting the arrhythmia episode that can include detecting a sustained episode if the arrhythmia duration exceeds a threshold, and detecting a non-sustained episode if the arrhythmia duration is below the threshold.

In Example 23, the subject matter of any one or more of Examples 16-22 optionally includes delivering a therapy to the patient in response to the detected arrhythmia episode.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
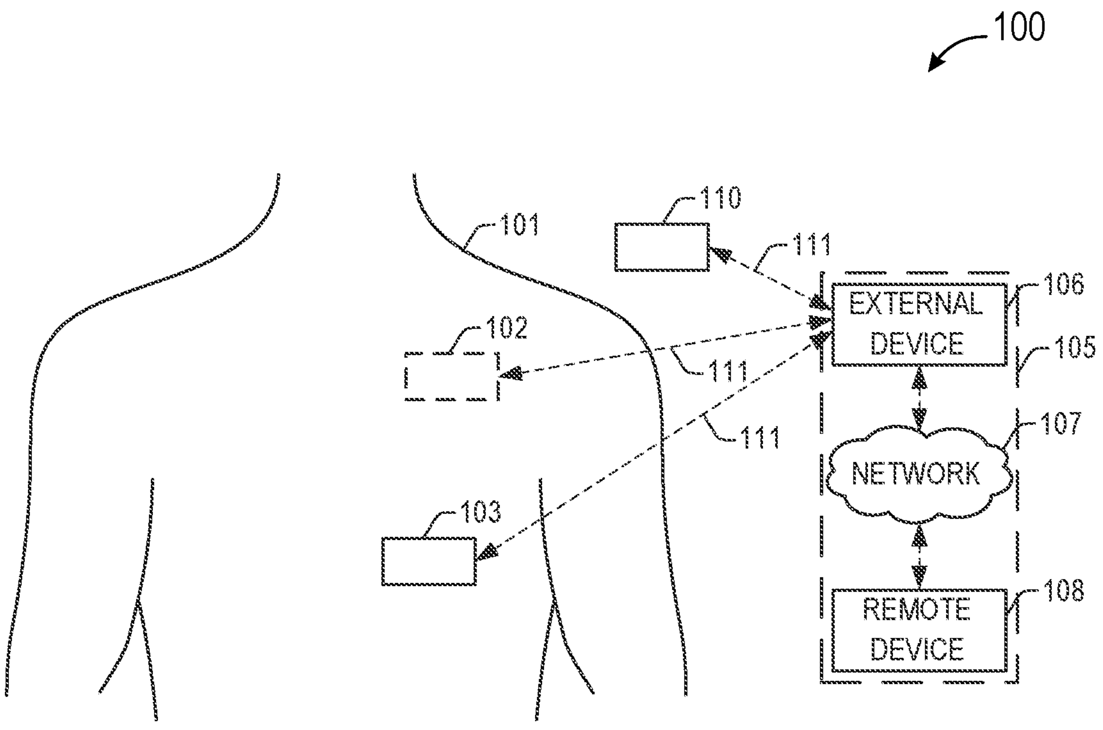
FIG. 1 illustrates generally an example of a patient management system and portions of an environment in which the system may operate.

Atrial tachyarrhythmia, such as AF or AFL, are characterized by fast atrial rate, and in some patients, increased variability of ventricular heart rate. In some patients, direct sensing of atrial activation rate with an electrode positioned in or near the atrium is not available or not feasible, such as patients not indicated for atrial lead implantation. A medical device, such as a single-chamber IMD with no dedicated atrial sensing/pacing lead, may detect AT based on ventricular heart rate, without direct sensing of atrial activity. However, confounding factors such as noise, motion artifacts, or cardiac rhythms other than the AT may be mistakenly detected as AT events. For example, during AFL, impulses from the atria are conducted to the ventricles through the atrio-ventricular node (AV node). Due primarily to its longer refractory period, the AV node may exert a protective effect on heart rate at the ventricle by blocking atrial impulses in excess of approximately 180 beats per minute (bpm). If an AFL rate is 300 bpm, a two-to-one (2:1) heart block may develop such that only half of the atrial impulses can be conducted to the ventricle, resulting in a ventricular rate of 150 bpm. In some cases, the refractoriness of the AV node may lead to irregular AV conductions, resulting in unstable ventricular rates.

Arrhythmia can be detected using a comparison of a signal metric generated from a physiologic signal to a detection criterion. To reduce computational burden, evaluation of the AT detection criterion may be performed periodically rather than on a beat-by-beat basis. For example, a boxcar function with a non-zero portion having a specified duration may be applied to a cardiac signal (e.g., surface electrocardiogram, or intracardiac electrogram) or other physiological signals to generate a signal segment, which can then be evaluated against AT detection criterion to determine if an arrhythmia is indicated. The boxcar function can slide in time to generate additional signal segments in consecutive time windows or timer periods, which can be similarly evaluated against the AT detection criterion. As such, the boxcar-based AT detection algorithm can effectually detect AT on a periodic basis.

Periodic assessment of AT detection criterion as does in boxcar-based AT detection can reduce computational burden. However, in some cases, the boxcar-based detection can be overly sensitive to noise or transient stabilization of heart rate (i.e., reduced variability in heart rate), causing inappropriate or unnecessary declarations of arrhythmia termination. For example, when an underlying AT event sustains for an extended period of time but the heart rate temporarily stabilizes, or intermittent noise or interferences are introduced and sensed by the sensing circuitry of the device, the detection algorithm may repeatedly detect arrhythmia termination of the present episode followed by, in just a short time interval, arrhythmia onset of the next AT episode, instead of detecting a "long" AT episode that would have more accurately reflected the underlying sustained AT event (e.g., one that may last for an hour). Consequently, a multitude of superfluous "short" AT episodes are detected, temporally interspersed with gaps as short as the duration of a boxcar function (e.g., 2-5 minutes). Because a "long" sustained AT episode generally may have different clinical implications than "short" AT episodes (including, for example, AT diagnostics such as AT sustainability and AT burden, and AT treatment regimens such as device therapy or antiarrhythmic drugs), inappropriate or unnecessary detections of arrhythmia termination may adversely impact treatment and patient outcome. Additionally, as the device-detected arrhythmia episodes are generally processed to produce respective episode summaries and the episode data and summaries are to be stored separately in device memory, the superfluous arrhythmia episodes may unnecessarily take up a significant amount of device computational and storage resources. Further, as the arrhythmia episode data may routinely be reviewed by a clinician or other human experts, the superfluous arrhythmia episodes can substantially increase human burden of reviewing and/or adjudicating such episodes as well as healthcare cost associated with patient management.

The present inventors have recognized a challenge in device-based arrhythmia detection, particularly a boxcar-based arrhythmia detector that detects repetitive and superfluous arrhythmia episodes (e.g., AT episode) from a long and sustained underlying arrhythmia event. The present inventors have recognized that such superfluous AT episodes may be caused by temporary heart rate stabilization or intermittent noise that inappropriately or unnecessarily trigger AT determination. The present inventors further recognized that a significant amount of consecutive short AT episodes (separated by a short time gap in between) are true positive AT episodes with similar arrhythmia characteristics, suggesting that these consecutive AT episodes could have been algorithmically detected as belong to one continuous episode, such that device computational and storage resources can be saved, and human workload of episode review can be justifiably reduced.

Disclosed herein are systems, devices, and methods that can improve detection of cardiac arrhythmias, such as AT. An exemplary system includes an arrhythmia detector circuit that can receive physiologic information sensed from a patient over time, detect an arrhythmia onset when the physiologic information during a first time period satisfies an onset condition, and in response to the detected arrhythmia onset, detect an arrhythmia termination when the physiologic information during a second time period, subsequent to and longer than the first time period, satisfies an exit condition. An arrhythmia episode can be detected based on an arrhythmia duration between the detected onset and termination. The detected sustained arrhythmia episode can be provided to a user or a processor for further processing.

The systems, devices, and methods discussed in this document may improve the medical technology of device-based arrhythmia detection and prevention of worsening of cardiac function. Although alternative solutions such as reducing detection sensitivities (e.g., a threshold for detecting unstable heart rates in a boxcar function) may also help reduce the chance of detecting superfluous short AT episodes, such solutions may nevertheless miss actual short-lived AT arrhythmia episodes, resulting in lack of treatment or untimely treatment, or unnecessary or inappropriate treatments. In contrast, the boxcar-based AT detection that uses distinct onset and termination conditions and physiologic data with distinct lengths for detecting respectively arrhythmia onset and termination, as discussed in this document, can advantageously enhance the AT detection performance and functionality of an implantable medical device. For example, in accordance with an example described in this document, a more stringent arrhythmia termination or exit condition can make it more "difficult" for a detected ongoing AT episode to exit or terminate, thereby promoting detection of a longer episode. Additionally, instead of adjusting a parameter (e.g., sensitivity threshold) within a boxcar function, longer physiologic data (e.g., two or more consecutive time windows) are used to detect AT termination than the physiologic data used for detecting AT onset. The arrhythmia detection systems and methods described in this document can avoid or reduce superfluous discrete AT episodes and promote detection of sustained AT episode, while at the same time reduce under-detections, such that the overall detection sensitivity can be improved with little to no additional cost or system complexity. With less redundant detections of a long and sustained underlying AT event, device computation and storage resources can be saved, human workload of reviewing and/or adjudicating the AT episodes can be lessened, healthcare cost associated with patient management can be reduced, and clinical utility of the heart rate-based AT detection may be improved.

In some examples, the arrhythmia detection systems and methods described in this document can be used to aggregate multiple short arrhythmia episodes (e.g., AT episodes) detected by a medical device. Such short arrhythmia episodes, which are characterized by short arrhythmia durations and are separated in time by short time gaps, can be repetitive and superfluous detections from a long and sustained underlying arrhythmia event. By aggregating multiple short arrhythmia episodes into one longer episode, less device storage is required, and human workload of episode review can be reduced.

In some examples, existing system performance can be maintained (e.g., high arrhythmia detection sensitivity and specificity, etc.) using lower cost or less obtrusive systems, apparatus, and methods. For example, because the system or device does not require direct sensing of atrial activity, the system complexity and implementation cost may be reduced. It may particularly be beneficial for patient not indicated for atrial lead implantation either for atrial activity sensing or for atrial pacing. Moreover, the arrhythmia detection discussed in this document may make more efficient use of device memory by storing information such as timings of AT onset and termination, which are clinically relevant to treatment and AT patient management. With improved AT detection, fewer alarms are provided, battery life can be extended, fewer unnecessary drugs and procedures may be scheduled, prescribed, or provided, and an overall system cost and power savings may be realized in contrast to existing medical devices and systems.

Although this document focuses on AT detection, it should be appreciated by one skilled in the art that this is by way of example and not by way of limitation. The systems, devices, and methods of arrhythmia onset and termination detection, in accordance with various examples described in this document, may be applicable to other arrhythmias or cardiac events including, for example, ventricular tachycardia, ventricular fibrillation, atrial or ventricular bradycardia, supraventricular tachycardia, among others. The method or techniques described in this document may be implemented in various ambulatory (e.g., implantable, wearable, or holdable) or stationary devices or medical systems.

FIG. 1 illustrates an example patient management system 100 and portions of an environment in which the patient management system 100 may operate. The patient management system 100 can perform a range of activities, including remote patient monitoring and diagnosis of a disease condition. Such activities can be performed proximal to a patient 101, such as in a patient home or office, through a centralized server, such as in a hospital, clinic, or physician office, or through a remote workstation, such as a secure wireless mobile computing device.

The patient management system 100 can include one or more ambulatory medical devices, an external system 105, and a communication link 111 providing for communication between the one or more ambulatory medical devices and the external system 105. The one or more ambulatory medical devices can include an implantable medical device (IMD) 102, a wearable medical device 103, or one or more other implantable, leadless, subcutaneous, external, wearable, or ambulatory medical devices configured to monitor, sense, or detect information from, determine physiologic information about, or provide one or more therapies to treat various conditions of the patient 101, such as one or more cardiac or non-cardiac conditions (e.g., dehydration, sleep disordered breathing, etc.).

In an example, the implantable medical device 102 can include one or more traditional cardiac rhythm management devices implanted in a chest of a patient, having a lead system including one or more transvenous, subcutaneous, or non-invasive leads or catheters to position one or more electrodes or other sensors (e.g., a heart sound sensor) in, on, or about a heart or one or more other position in a thorax, abdomen, or neck of the patient 101. In another example, the implantable medical device 102 can include a monitor implanted, for example, subcutaneously in the chest of patient 101, the implantable medical device 102 including a housing containing circuitry and, in certain examples, one or more sensors, such as a temperature sensor, etc.

The implantable medical device 102 can include an assessment circuit configured to detect or determine specific physiologic information of the patient 101, or to determine one or more conditions or provide information or an alert to a user, such as the patient 101 (e.g., a patient), a clinician, or one or more other caregivers or processes. The implantable medical device 102 can alternatively or additionally be configured as a therapeutic device configured to treat one or more medical conditions of the patient 101. The therapy can be delivered to the patient 101 via the lead system and associated electrodes or using one or more other delivery mechanisms. The therapy can include delivery of one or more drugs to the patient 101, such as using the implantable medical device 102 or one or more of the other ambulatory medical devices, etc. In some examples, therapy can include cardiac resynchronization therapy for rectifying dyssynchrony and improving cardiac function in heart failure patients. In other examples, the implantable medical device 102 can include a drug delivery system, such as a drug infusion pump to deliver drugs to the patient for managing arrhythmias or complications from arrhythmias, hypertension, or one or more other physiologic conditions. In other examples, the implantable medical device 102 can include one or more electrodes configured to stimulate the nervous system of the patient or to provide stimulation to the muscles of the patient airway, etc.

The wearable medical device 103 can include one or more wearable or external medical sensors or devices (e.g., automatic external defibrillators (AEDs), Holter monitors, patch-based devices, smart watches, smart accessories, wrist- or finger-worn medical devices, such as a finger-based photoplethysmography sensor, etc.).

The external system 105 can include a dedicated hardware/software system, such as a programmer, a remote server-based patient management system, or alternatively a system defined predominantly by software running on a standard personal computer. The external system 105 can manage the patient 101 through the implantable medical device 102 or one or more other ambulatory medical devices connected to the external system 105 via a communication link 111. In other examples, the implantable medical device 102 can be connected to the wearable medical device 103, or the wearable medical device 103 can be connected to the external system 105, via the communication link 111. This can include, for example, programming the implantable medical device 102 to perform one or more of acquiring physiologic data, performing at least one self-diagnostic test (such as for a device operational status), analyzing the physiologic data, or optionally delivering or adjusting a therapy for the patient 101. Additionally, the external system 105 can send information to, or receive information from, the implantable medical device 102 or the wearable medical device 103 via the communication link 111. Examples of the information can include real-time or stored physiologic data from the patient 101, diagnostic data, such as detection of patient hydration status, hospitalizations, responses to therapies delivered to the patient 101, or device operational status of the implantable medical device 102 or the wearable medical device 103 (e.g., battery status, lead impedance, etc.). The communication link 111 can be an inductive telemetry link, a capacitive telemetry link, or a radio-frequency (RF) telemetry link, or wireless telemetry based on, for example, "strong" Bluetooth or IEEE 802.11 wireless fidelity "Wi-Fi" interfacing standards. Other configurations and combinations of patient data source interfacing are possible.

The external system 105 can include an external device 106 in proximity of the one or more ambulatory medical devices, and a remote device 108 in a location relatively distant from the one or more ambulatory medical devices, in communication with the external device 106 via a communication network 107. Examples of the external device 106 can include a medical device programmer. The remote device 108 can be configured to evaluate collected patient or patient information and provide alert notifications, among other possible functions. In an example, the remote device 108 can include a centralized server acting as a central hub for collected data storage and analysis. The server can be configured as a uni-, multi-, or distributed computing and processing system. The remote device 108 can receive data from multiple patients. The data can be collected by the one or more ambulatory medical devices, among other data acquisition sensors or devices associated with the patient 101. The server can include a memory device to store the data in a patient database. The server can include an alert analyzer circuit to evaluate the collected data to determine if specific alert condition is satisfied. Satisfaction of the alert condition may trigger a generation of alert notifications, such to be provided by one or more human-perceptible user interfaces. In some examples, the alert conditions may alternatively or additionally be evaluated by the one or more ambulatory medical devices, such as the implantable medical device. By way of example, alert notifications can include a Web page update, phone or pager call, E-mail, SMS, text or "Instant" message, as well as a message to the patient and a simultaneous direct notification to emergency services and to the clinician. Other alert notifications are possible. The server can include an alert prioritizer circuit configured to prioritize the alert notifications. For example, an alert of a detected medical event can be prioritized using a similarity metric between the physiologic data associated with the detected medical event to physiologic data associated with the historical alerts.

The remote device 108 may additionally include one or more locally configured clients or remote clients securely connected over the communication network 107 to the server. Examples of the clients can include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning. In addition to generating alert notifications, the remote device 108, including the server and the interconnected clients, may also execute a follow-up scheme by sending follow-up requests to the one or more ambulatory medical devices, or by sending a message or other communication to the patient 101 (e.g., the patient), clinician or authorized third party as a compliance notification.

The communication network 107 can provide wired or wireless interconnectivity. In an example, the communication network 107 can be based on the Transmission Control Protocol/Internet Protocol (TCP/IP) network communication specification, although other types or combinations of networking implementations are possible. Similarly, other network topologies and arrangements are possible.

One or more of the external device 106 or the remote device 108 can output the detected medical events to a system user, such as the patient or a clinician, or to a process including, for example, an instance of a computer program executable in a microprocessor. In an example, the process can include an automated generation of recommendations for anti-arrhythmic therapy, or a recommendation for further diagnostic test or treatment. In an example, the external device 106 or the remote device 108 can include a respective display unit for displaying the physiologic or functional signals, or alerts, alarms, emergency calls, or other forms of warnings to signal the detection of arrhythmias. In some examples, the external system 105 can include an external data processor configured to analyze the physiologic or functional signals received by the one or more ambulatory medical devices, and to confirm or reject the detection of arrhythmias. Computationally intensive algorithms, such as machine-learning algorithms, can be implemented in the external data processor to process the data retrospectively to detect cardia arrhythmias.

Portions of the one or more ambulatory medical devices or the external system 105 can be implemented using hardware, software, firmware, or combinations thereof. Portions of the one or more ambulatory medical devices or the external system 105 can be implemented using an application-specific circuit that can be constructed or configured to perform one or more functions or can be implemented using a general-purpose circuit that can be programmed or otherwise configured to perform one or more functions. Such a general-purpose circuit can include a microprocessor or a portion thereof, a microcontroller or a portion thereof, or a programmable logic circuit, a memory circuit, a network interface, and various components for interconnecting these components. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. "Sensors" can include electronic circuits configured to receive information and provide an electronic output representative of such received information.

The therapy device 110 can be configured to send information to or receive information from one or more of the ambulatory medical devices or the external system 105 using the communication link 111. In an example, the one or more ambulatory medical devices, the external device 106, or the remote device 108 can be configured to control one or more parameters of the therapy device 110. The external system 105 can allow for programming the one or more ambulatory medical devices and can receives information about one or more signals acquired by the one or more ambulatory medical devices, such as can be received via a communication link 111. The external system 105 can include a local external implantable medical device programmer. The external system 105 can include a remote patient management system that can monitor patient status or adjust one or more therapies such as from a remote location.

Figure 2:
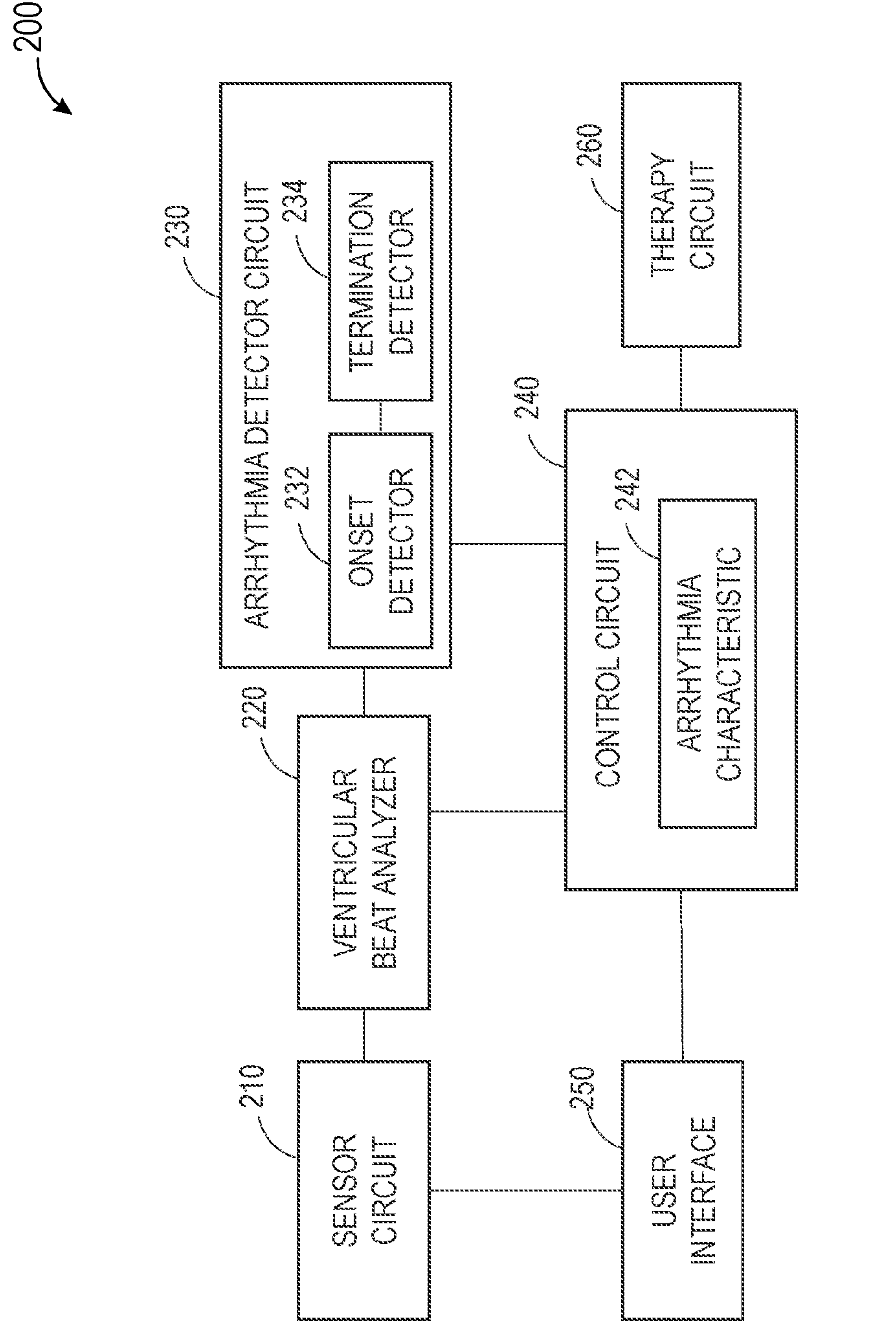
FIG. 2 illustrates generally an example of an arrhythmia detection system configured to detect an arrhythmia episode, such as an AT episode.

FIG. 2 illustrates generally an example of an arrhythmia detection system 200 configured to detect an arrhythmia episode, such as an AT episode. The arrhythmia detection system 200 may include one or more of a sensor circuit 210, a ventricular beat analyzer circuit 220, an arrhythmia detector circuit 230, a controller circuit 240, and a user interface unit 250. The arrhythmia detection system 200 may include an optional therapy circuit 260. At least a portion of the system 200, such as one or more of the ventricular beat analyzer circuit 220, the arrhythmia detector circuit 230, the control circuit 240, or the therapy circuit 260, may be included in the IMD 102, the wearable medical device 103, the therapy device 110, or the external system 105 (e.g., the external device 106). In an example, the ventricular beat analyzer circuit 220, the arrhythmia detector circuit 230, the control circuit 240, and the therapy circuit 260 are all included in the IMD 102, or are all included in the wearable medical device 103. In another example, the sensor circuit 210 is included in the IMD 102 or the wearable medical device 103, and the rest of the circuits are in the external system 105. In yet another example, a first portion of the circuits of the system 200 are in the IMD 102 or the wearable medical device 103, and a second portion of the circuits of the system 200 are in the external system 105.

The sensor circuit 210 may include a sense amplifier circuit to sense a physiologic signal from a patient via one or more implantable, wearable, or otherwise ambulatory sensors or electrodes associated with the patient. The sensed physiologic signal may contain information about pulsatile cardiac activity, such as heart rate or pulse rate. Examples of the physiologic signals may include surface electrocardiography (ECG) such as sensed from electrodes on the body surface, subcutaneous ECG such as sensed from electrodes placed under the skin, intracardiac electrogram (EGM) sensed from the one or more electrodes on a lead system, thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal such as sensed by an ambulatory accelerometer or acoustic sensors, physiologic response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others. The sensor circuit 210 may include one or more other sub-circuits to digitize, filter, or perform other signal conditioning operations on the received physiologic signal.

In some examples, the physiologic signals may be stored in a storage device such as an electronic medical record system. The sensor circuit 210 may retrieve a physiologic signal from the storage device in response to a command signal that is provided by a system user, or automatically generated in response to occurrence of a specific event.

The ventricular beat analyzer circuit 220 may be coupled to the sensor circuit 210 to detect ventricular beats and assess ventricular activity, such as to evaluate ventricular rate stability (VRS) using the physiologic information such as provided by the sensor circuit 210. In an example, the physiologic information includes a cardiac signal representative of ventricular electrical or mechanical activation. In an example, the VRS may be computed using ventricular rates or cardiac cycle lengths measured form an electrophysiological signal, such as an ECG, a subcutaneous ECG, or an intracardiac EGM. Alternatively, ventricular rate may be detected using a mechano-physiological signal, such as a heart sound signal sensed using an accelerometer or a microphone sensor, cardiac or thoracic impedance signal, or a blood pressure signal, among other sensors. The VRS may be computed using a relative difference in ventricular cycle length between cardiac cycles, such as consecutive cardiac cycles, that measured from the cardiac signal, a variance, a standard deviation, a metric derived from a histogram or a statistical distribution of ventricular cycle length over multiple cardiac cycles, among other variability measures or second-order statistics known in the art.

The arrhythmia detector circuit 230 may detect, in a plurality of time windows, respective AT indications using portions of physiologic information received from the patient 101, such as respective physiologic signal segments in the distinct time windows. The time windows can be consecutive in time without overlapping one another. The signal segments may be generated by applying boxcar functions to the received physiologic signal. A boxcar function is a data window with non-zero portion equal to the distinct time windows. In an example, the time windows have the same duration (T). The duration T can be user programmable, such as via the user interface unit 250. By way of example and not limitation, the duration T is approximately one to five minutes. In an example, the duration T is approximately two minutes. The duration T can be a fixed value. Alternatively, in some examples, the control circuit 240 may automatically adjust the duration T using one or more parameters computed from the previous signal segments, such as heart rate or heart rate stability.

The arrhythmia detector circuit 230 can include an onset detector 232 and a termination detector 234. The onset detector 232 can detect an arrhythmia onset (e.g., AT onset) when the physiologic information during a first time period satisfies an onset condition. In an example, the first time period can be a time window ($W_0$) having the duration T, as discussed above. The onset condition can include an initial criterion and a confirmation criterion. An arrhythmia onset is deemed detected when the physiologic information in the first time period (e.g., the time window $W_0$) satisfies both the initial detection criterion (IC) and the confirmation criterion (CC). Such onset condition ("ONSET") can be expressed using the following logic formula:

$$\text{ONSET}=(W_0 \text{ satisfies IC}) \text{ AND } (W_0 \text{ satisfies CC}) \quad (1)$$

Figure 3:
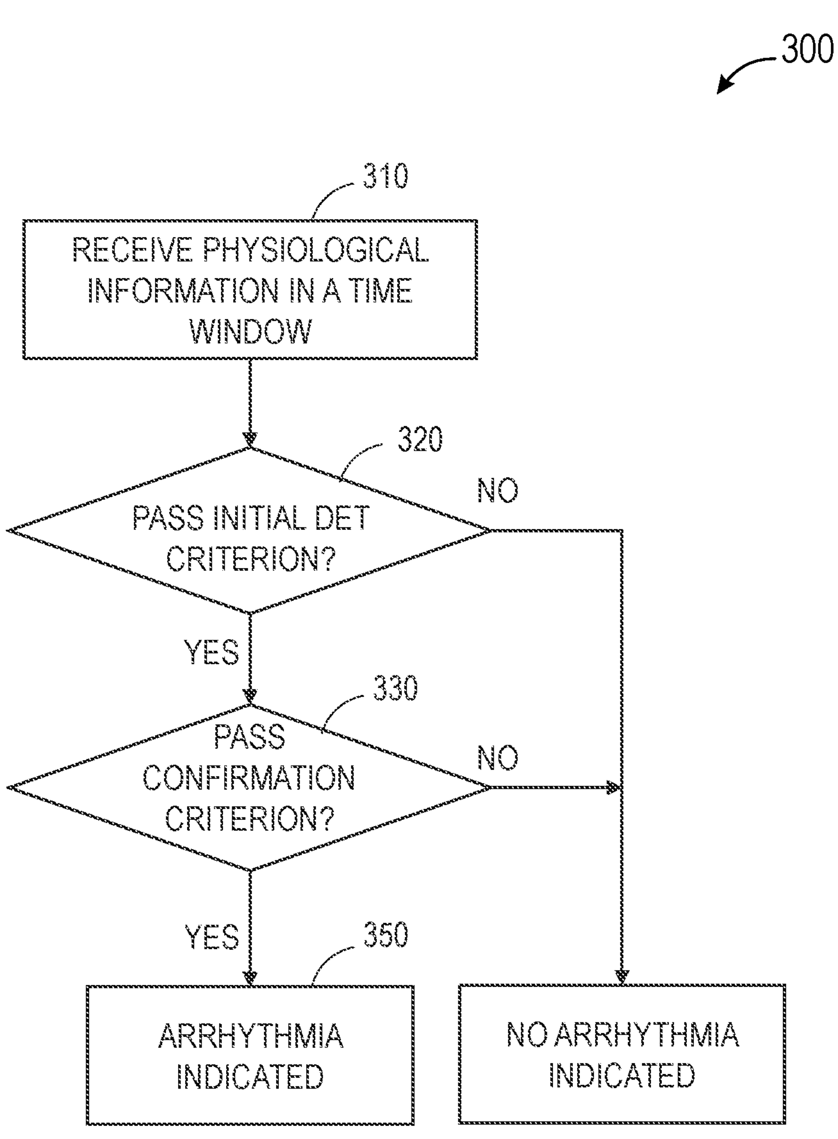
FIG. 3 is a flowchart illustrating a method for detecting an AT indication using physiologic information received from a patient.

Referring now to FIG. 3, a flowchart therein illustrates a method 300 for detecting an AT indication using physiologic information received from a patient. In an example of boxcar-based arrhythmia detection where the receive physiologic information is analyzed in each of a series of time windows, the method 300 may be used to determine whether respective physiologic information in each of those time windows indicates arrhythmia (e.g., AT) presence or absence. An arrhythmia episode (e.g., an AT episode) can be detected based on the detected arrhythmia indications in respective time windows.

At 310, physiologic information in a time window, such as a physiological signal segment in a boxcar function of a duration T, is received. The received physiologic information can then be first checked against an initial detection criterion at 320. If the physiologic information in the window fails the initial detection criterion, then it can be decided at 340 that no arrhythmia indication is detected in the present time window. If the physiologic information in the window satisfies the initial detection criterion, the physiologic information can be further checked against a confirmation criterion at 330. The confirmation criterion can be more specific to the arrhythmia of interest (e.g., AT) than the initial detection criterion, such that a higher detection specificity (or a lower false positive rate) can be achieved with the confirmation than without the confirmation process. If the physiologic information also satisfies the confirmation criterion, then an arrhythmia indication is detected in the present time window at 350; if the physiologic information fails the confirmation criterion, then no arrhythmia indication is detected at 340.

Different physiologic information may be used for initial detection (320 of FIG. 3) and for confirmation (330 of FIG. 3). In an example, the onset detector 232 can generate a first signal metric $X_0$ and a different second signal metric $Y_0$ from the physiologic information in the time window $W_0$, use the first signal metric $X_0$ for initial detection 320, and use the second signal metric $Y_0$ for confirmation 330. When the method 300 is used to detect AT indications, the first signal metric $X_0$ can include atrial rate or heart (ventricular) rate variability determined from the physiologic information in the time window, and the initial detection criterion at 320 can be the atrial rate or the heart rate variability exceeding respective threshold values. The second signal metric $Y_0$ can include physiological signal morphology features. For example, the confirmation criterion at 330 may include a morphological similarity metric between the physiological signal segment in the time window and a morphology template (such as an AT template, or a normal sinus rhythm template) in comparison to a patient-specific similarity threshold. Examples of the similarity measure may include a correlation or a distance in a signal feature space. In an example, the physiologic information in the window passes the confirmation criterion at 330 if the morphological similarity to the AT template exceeds a threshold.

The second signal metric $Y_0$ used for confirmation at 330 can include heart rate patterns or organizational features. In various examples, AT indications may be confirmed using a statistical measure of ventricular rate or ventricular cycle length. One example of the statistical measure includes a ventricular rate pattern of consecutive decrease in ventricular rate. The ventricular rate pattern includes a pair of consecutive ventricular rate changes. Both ventricular rate changes are negative, referred to as a "double decrement" ventricular rate pattern. A double-decrement ratio, which represents a prevalence of the double decrement ventricular rate pattern over a specific time period or over a plurality of ventricular beats, may be computed, and used to detect AT (e.g., AF), or to distinguish AT from ectopic beats. The arrhythmia detector circuit 230 may determine a count of double-decrement beat pattern, or a double-decrement ratio. Such a baseline double-decrement pattern of ventricular rate may distinguish frequent premature ventricular contractions (PVCs) from an AT event, because PVCs alone typically do not produce double decrement patterns in ventricular rate. Krueger et al. U.S. patent application Ser. No. 14/825,669, entitled "ATRIAL FIBRILLATION DETECTION USING VENTRICULAR RATE VARIABILITY," refers to double decrement pattern in ventricular heart rate and its use in atrial arrhythmia detection, the disclosure of which is incorporated by reference herein in its entirety.

Another example of the statistical measure includes a ventricular rate cluster, represented by a statistical distribution or a histogram of ventricular rate or cycle length over multiple cardiac cycles. The ventricular rate cluster indicates regularity of ventricular rates of cardiac cycle lengths. Patients with AF are typically presented with irregular ventricular contractions. However, premature atrial contractions (PACs) may occur at irregular intervals. When PACs conduct to the ventricle, they may produce irregular ventricular rates, resulting in different ventricular clusters than AF. As such, the ventricular rate clusters may be used to distinguish frequent PACs from an AF event. Perschbacher et al. U.S. patent application Ser. No. 15/864,953 entitled "ATRIAL FIBRILLATION DISCRIMINATION USING HEART RATE CLUSTERING," refers to histogram clusters of ventricular rates and their use in discriminating between AF and non-AF events, the disclosure of which is incorporated by reference herein in its entirety.

Yet another example of the statistical measure includes a metric representing the occurrence of various beat patterns of the cycle lengths or heart rates. For example, the beat pattern may include a number or percentage of consecutive heart beats with each time window (e.g., a 2-minute time windows) that are within +/− bpm. In an example, the statistical measure includes an atrioventricular (AV) conduction block metric indicating a presence or degree of conduction abnormality during a sinus rhythm, such as a Wenckebach score representing the prevalence of Wenckebach block over a time period. Examples of the Wenckebach detector may be based on a repetitiveness indictor of various beat patterns of the cycle lengths or heart rates, such as discussed in Perschbacher et al. U.S. patent application Ser. No. 15/786,824 entitled "SYSTEMS AND METHODS FOR ARRHYTHMIA DETECTION," the disclosure of which is incorporated by reference herein in its entirety. Other examples of the statistical measure may include a signal morphology metric representing regularity of ventricular depolarization signal morphology during sinus rhythm, or a signal quality metric such as a signal-to-noise (SNR). The signal quality or signal morphology indicator may differentiate AT from noise.

Referring back to FIG. 2, in response to the detected arrhythmia onset, the termination detector 234 can detect an arrhythmia termination (e.g., AT termination) when the physiologic information during a second time period, subsequent to and longer than the first time period, satisfies an exit condition different than the onset condition. In an example, the second time period includes two or more consecutive time windows subsequent to the first time window $W_0$. The two or more consecutive time windows each may have a duration substantially equal to the duration of the first time window $W_0$. The termination detector 234 can detect an arrhythmia termination when respective physiologic information in each of the two or more consecutive time windows separately satisfy the exit condition.

The exit condition can include an initial criterion and a confirmation criterion, as illustrated in FIG. 3, applied to each of the two or more consecutive time windows (e.g., two consecutives $W_n$ and $W_{n+1}$). In an example, the termination detector 234 can detect the arrhythmia termination when the physiologic information in at least one of the two or more consecutive windows (e.g., at least one of $W_n$ or $W_{n+1}$) fails the initial criterion (IC), or when the respective physiologic information in each of the second two or more consecutive windows (e.g., each of $W_n$ and $W_{n+1}$) separately fails the confirmation criterion (CC). Such exit condition ("EXIT") can be expressed using the following logic formula:

$$\text{EXIT}=(W_n \text{ fails IC}) \text{ OR } (W_{n+1} \text{ fails IC}) \text{ OR } ((W_n \text{ fails CC}) \text{ AND } (W_{n+1} \text{ fails CC})) \quad (2)$$

As similarly discussed above with respect to the onset detector 232, the termination detector 234 may use different physiologic information for initial detection and confirmation phases of detecting arrhythmia termination. When the termination detector 234 uses two consecutive time windows $W_n$ or $W_{n+1}$, the termination detector 234 can generate a first signal metric $X_n$ and a different second signal metric $Y_n$ from the physiologic information in time window $W_n$, use the first signal metric $X_n$ for initial detection 320, and use the second signal metric $Y_n$ for confirmation 330. Similarly, the termination detector 234 can generate a first signal metric $X_{n+1}$ and a different second signal metric $Y_{n+1}$ from the physiologic information in time window $W_{n+1}$, use the first signal metric $X_{n+1}$ for initial detection 320, and use the second signal metric $Y_{n+1}$ for confirmation 330. The first signal metrics $X_n$ and $X_{n+1}$ can each include atrial rate or heart (ventricular) rate variability. The second signal metrics $Y_n$ and $Y_{n+1}$ can include physiological signal morphology features, or a heart rate pattern or organizational feature based on statistics of ventricular rate or ventricular cycle length, such as a "double decrement" ventricular rate pattern, a ventricular rate cluster, a Wenckebach score, as described above. An example of the detecting AT termination using two consecutive time windows are discussed below with reference to FIG. 4.

In some examples, the arrhythmia detection used by the arrhythmia detector circuit 230 may be used to aggregate multiple short arrhythmia episodes (e.g., AT episodes) detected by a medical device. Such short arrhythmia episodes, which are characterized by short arrhythmia durations (e.g., less than a specified duration threshold) and are separated in time by short time gaps (e.g., 2-5 minutes), can be repetitive and superfluous detections from a long and sustained underlying arrhythmia event. For example, termination detection as described above may be performed on each of the short arrhythmia episodes using the termination detector 234 to determine if an exit condition is satisfied in accordance with the logic formula (2). If the exit condition is not satisfied, then the present short arrhythmia episode can be aggregated with the immediate next short arrhythmia episode. This process can be continued until the exit condition is satisfied in a short arrhythmia episode. By aggregating multiple short arrhythmia episodes into one longer episode, less device storage is required, and human workload of episode review can be reduced.

The arrhythmia detector circuit 230 can determine an arrhythmia duration between the detected arrhythmia onset and the detected arrhythmia termination, and detect a sustained arrhythmia episode based on the arrhythmia duration. In an example, an arrhythmia episode is detected as a sustained arrhythmia episode if the arrhythmia duration exceeds a duration threshold, or as a non-sustained arrhythmia episode if the arrhythmia duration is below the duration threshold. By way of example and not limitation, the duration threshold is approximately ten minutes. In an example, the duration threshold is programmable, and can be set or adjusted by a user such as via the user interface unit 250.

The control circuit 240 may control the arrhythmia detection in response to a detected event or a user command. In an example of detecting AT, the AT onset detection can be triggered by the ventricular beats satisfying a specific condition, and controllably withhold AT detection when an exit conditions is satisfied and AT terminates. In an example, the control circuit 240 may monitor the VRS, and trigger the arrhythmia detector circuit 230 to detect respective AT indications within the distinct time windows when the VRS satisfies an instability criterion indicating unstable ventricular rate.

The control circuit 240 may generate arrhythmia characteristics 242 from the detected arrhythmia episode. In an example of detecting an AT episode, the arrhythmia characteristics 242 can include AT duration, AT burden, among other AT characteristics. In an example, the AT characteristics can be generated using the AT indications detected from the plurality of distinct time windows. The control circuit 240 can store portions of the received physiologic information in a memory circuit, such as the signal segments corresponding to the AT indications indicating a presence of AT. In another example, a portion of the received physiologic information between the detected onset and the detected termination of the AT episode can be stored in the memory circuit.

Portions of the system 200, such as one or more of the ventricular beat analyzer circuit 220, the arrhythmia detector circuit 230, or the control circuit 240, may respectively include circuit sets comprising one or more other circuits or sub-circuits. The circuits or sub-circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

In various examples, portions of the functions of the ventricular beat analyzer circuit 220, the arrhythmia detector circuit 230, and the control circuit 240 may be implemented as a part of a microprocessor circuit. The microprocessor circuit may be a dedicated processor such as a digital signal processor, application specific integrated circuit (ASIC), microprocessor, or other type of processor for processing information including the physiologic signals received from the sensor circuit 210. Alternatively, the microprocessor circuit may be a general-purpose processor that may receive and execute a set of instructions of performing the functions, methods, or techniques described herein.

The user interface unit 250 may include an input device and an output device. In an example, at least a portion of the user interface unit 250 may be implemented in the external system 105. The input device may receive a user's programming input, such as the duration T of the time window, number of time windows used for detecting AT onset and for detecting AT termination, threshold values for the initial detection criterion and the confirmation criterion in FIG. 3, AT duration threshold, etc. The input device may include a keyboard, on-screen keyboard, mouse, trackball, touchpad, touch-screen, or other pointing or navigating devices. The input device may enable a system user to program the parameters used for sensing the physiologic signals, detecting the arrhythmias, and generating alerts, among others.

The output device may generate a human-perceptible presentation of the detected cardiac arrhythmia. The output device may include a display for displaying the sensed physiologic signal, intermediate measurements or computations such as VRS, AT indications in respective time durations, among others. The output unit may include a printer for printing hard copies of the detection information. The information may be presented in a table, a chart, a diagram, or any other types of textual, tabular, or graphical presentation formats. The presentation of the output information may include audio or other media format to alert the system user of the detected arrhythmic events. In an example, the output device may generate alerts, alarms, emergency calls, or other forms of warnings to signal the system user about the detected arrhythmic events.

The optional therapy circuit 260 may be configured to deliver a therapy to the patient in response to the detected cardiac arrhythmia, such as an AT episode. Examples of the therapy may include electrostimulation therapy delivered to the heart, a nerve tissue, other target tissues, a cardioversion therapy, a defibrillation therapy, or drug therapy. In some examples, the therapy circuit 260 may modify an existing therapy, such as adjust a stimulation parameter or drug dosage.

Figure 4:
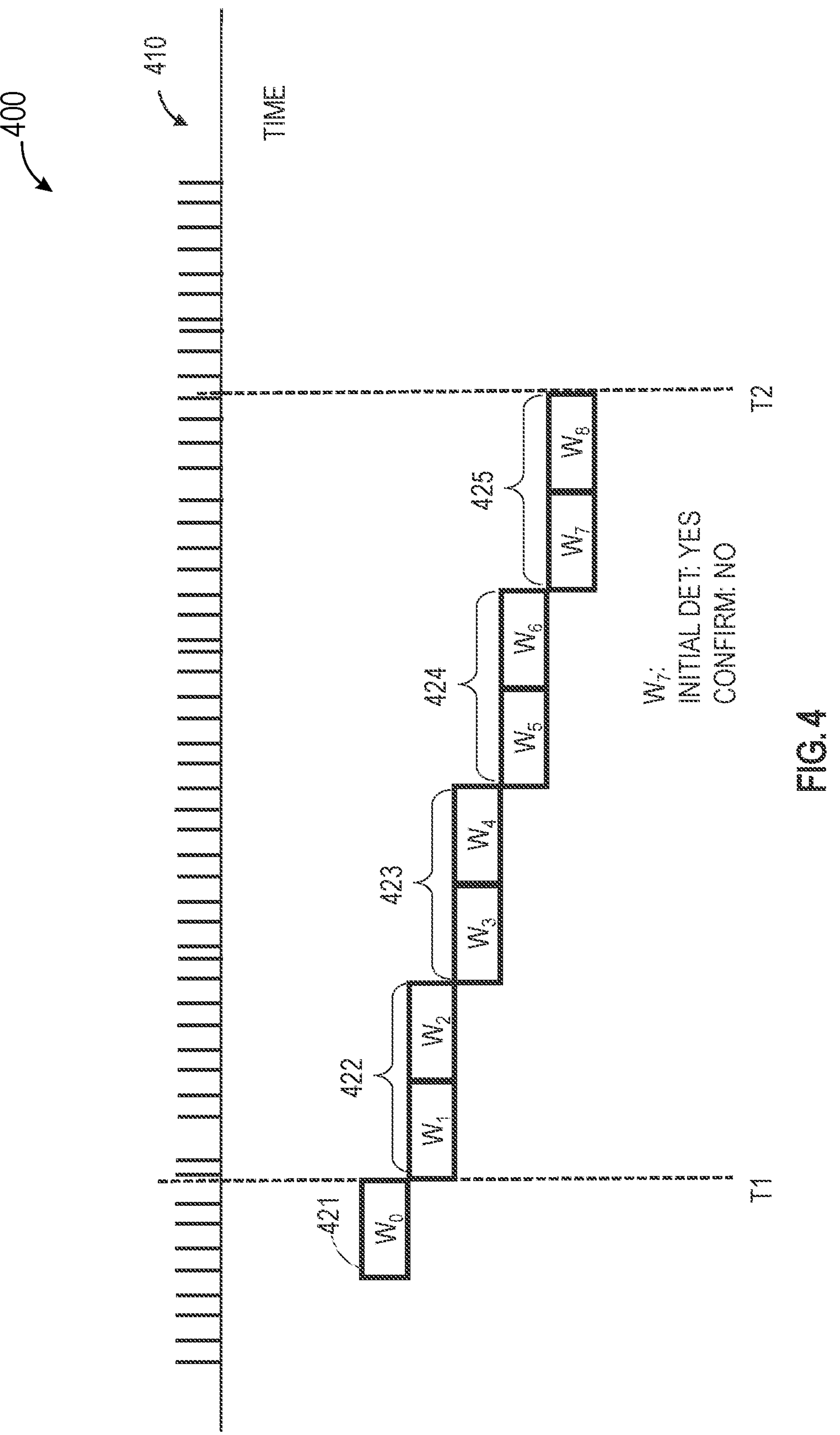
FIG. 4 is a timing diagram illustrating event timings in a boxcar-based AT detection process using multiple time windows.

FIG. 4 is a timing diagram 400 illustrating event timing in a boxcar-based AT detection from a cardiac signal 410 containing of ventricular beats information (shown as vertical bars). The ventricular beats may be detected and ventricular rate is analyzed using the ventricular beat analyzer circuit 220. The cardiac signal 410 may be partitioned into segments of boxcars or time windows having a specific duration T, which can be approximately two minutes in an example. The onset detector 232 can detect AT onset from a first time window $W_0$ 421 using a signal metric generated from the signal segment in the time window $W_0$, such as a ventricular rate variability, signal morphology, a ventricular rate pattern, ventricular rate cluster, or Wenckebach score, among other heart rate patterns or organizational features. As discussed above with reference to FIG. 3, the arrhythmia onset detection may include an initial detection and a confirmation process each involving respective different detection criteria, or respective different signal metrics that may be applied to the initial detection and confirmation.

In the illustrated example, the signal segment in $W_0$ passes both the initial detection criterion (IC) and the confirmation criterion (CC), thus satisfies the onset condition. Accordingly, an AT onset is declared at time T1, which can be the end of $W_0$ (as illustrated), or alternatively the beginning of $W_0$. In response to the AT onset detection, the control circuit 240 triggers the termination detector 234 to detect an arrhythmia termination using signal segments in window pair 422 consisting of two consecutive time windows $W_1$ and $W_2$ each having the same duration T as $W_0$. As discussed above with reference to FIG. 3, an AT termination may be declared if the signal segment in at least one of $W_1$ or $W_2$ fails the initial criterion (IC), or the signal segment of $W_1$ and the signal segment of $W_2$ both fail the confirmation criterion (CC). In this example, signal segments in the window pair 422 do not satisfy the AT termination condition; the termination detector 234 continues to detect AT termination in next window pair 423 consisting of consecutive time windows $W_3$ and $W_4$. The window pair 423 can be non-overlapping with the preceding window pair 422 (as shown). Alternatively, adjacent window pairs (such as 422 and 423) can overlap to each other by a specific time interval, such as one time window in an example. Signal segments in window pair 423 do not satisfy the AT termination condition; the termination detector 234 continues to detect AT termination in subsequent window pairs 424 (consisting of time windows $W_5$ and $W_6$) and 425 (consisting of time windows $W_7$ and $W_8$), until the AT termination condition is satisfied. In the illustrated example, for window pair 425 consisting of time windows $W_7$ and $W_8$, the termination detector 234 detects that the signal segment in $W_7$ satisfies the initial detection criterion (IC) but fails the confirmation criterion (CC). The termination detector 234 may further detect whether the signal segment in $W_8$ satisfies the IC and/or CC, and determine whether the window pair 425 satisfies the termination condition according to logic formula (2) above. The following table shows the AT termination decisions based on initial detection and confirmation results for time windows $W_7$ and $W_8$:

| $W_7$ (IC, CC) | $W_8$ (IC, CC) | $W_7$-$W_8$ pair triggers AT termination? |
|---|---|---|
| Y, N | Y, Y | AT continues |
| Y, N | Y, N | AT terminates |
| Y, N | N, Y | AT terminates |
| Y, N | N, N | AT terminates |

The detection status tuple in the table above (e.g., (Y, N)) indicates whether the signal segment in that time window passes ("Y") or fails ("N") the initial detection criterion (IC) and the confirmation criterion (CC). For example, a detection status (Y, N) for $W_8$ means that signal segment in $W_8$ passes IC but fails CC. In this example, if $W_8$ passes both the initial detection and confirmation (thus a detection status tuple (Y, Y)), then the window pair 425 does not satisfy the termination condition; and AT detection continues. If $W_8$ passes the initial detection but fails confirmation (thus a detection status tuple (Y, N)), then the window pair 425 satisfies termination condition, and AT terminates.

If the window pair 425 satisfies the termination condition, an AT termination is declared at time T2, which can be the end of $W_8$. The arrhythmia detector circuit 230 can determine an arrhythmia duration between the onset detection time T1 and the termination time T2. A sustained AT episode is detected if the arrhythmia duration exceeds a duration threshold, or as a non-sustained arrhythmia episode if the arrhythmia duration is below the duration threshold. The detected AT episode can be reported to a user, stored in a storage device, or output to a processor for further processing. In some examples, the AT duration may be used to determine patient AT burden, such as within a 24-hour period.

Figure 5:
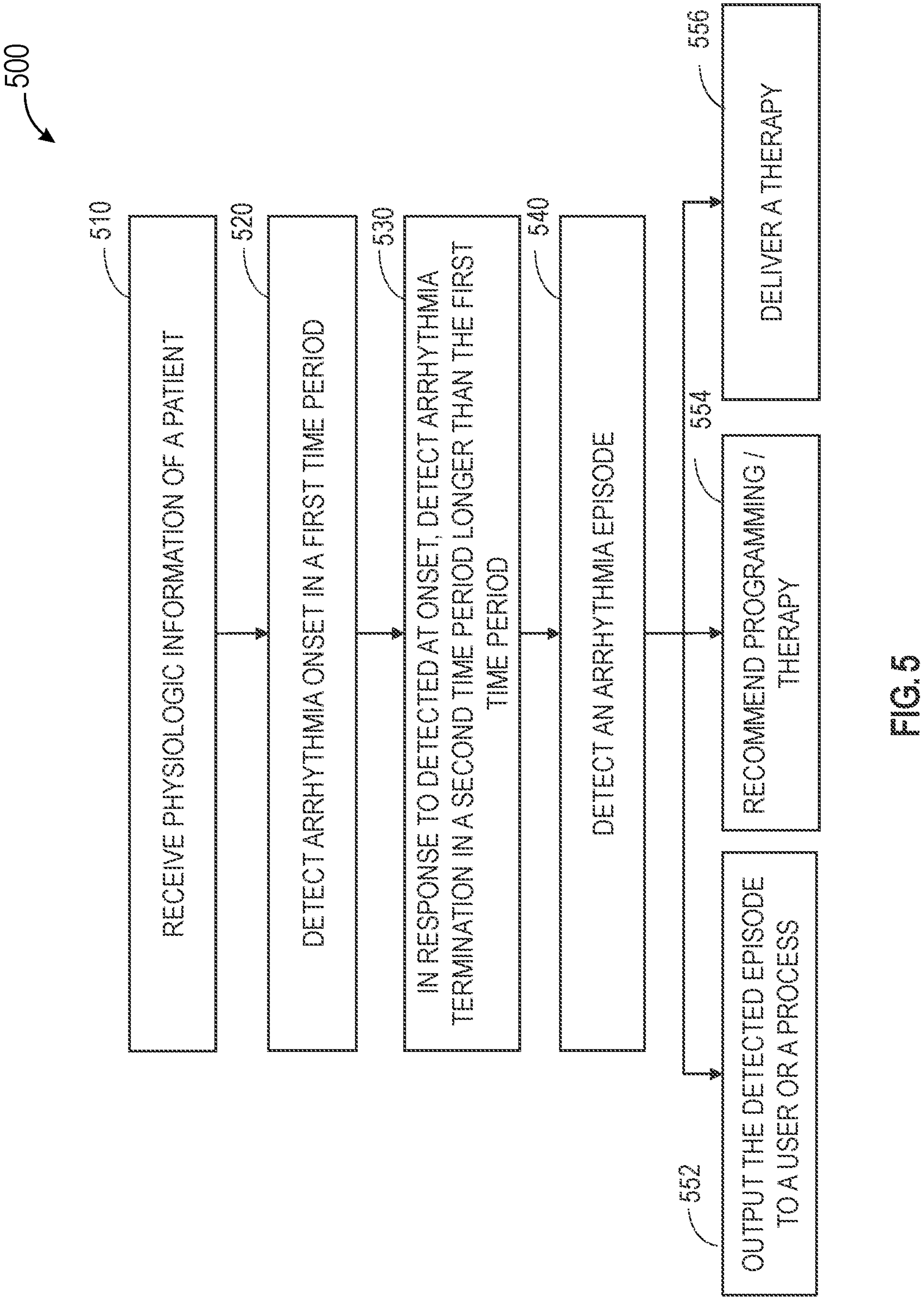
FIG. 5 is a flowchart illustrating an example of a method for detecting cardiac arrhythmia using multiple time windows.

FIG. 5 is a flowchart illustrating an example of a method 500 for detecting cardiac arrhythmia in a patient using multiple time windows. One non-limiting example of such arrhythmia that may be detected using method 500 is atrial tachyarrhythmia (AT), including, for example, atrial fibrillation (AF), atrial flutter (AFL), atrial tachycardia, paroxysmal supraventricular tachycardia (PSVT), among others. The method 500 may be implemented and executed in an ambulatory medical device such as an implantable or wearable device, or in a remote patient management system. In an example, the method 500 may be implemented in and executed by the IMD 102, the wearable medical device 103, the external system 105, or the arrhythmia detection system 200.

The method 500 commences at step 510, where physiologic information of a patient may be received. The physiologic information may include one or more physiologic signals sensed by one or more implantable, wearable, or otherwise ambulatory sensors. Examples of the physiologic signals may include cardiac electrical signals, such as ECG or EGM, or signals indicative of cardiac mechanical activity, such as pressure, impedance, heart sounds, or respiration signals. The sensed physiologic signal may be pre-processed, including amplification, digitization, filtering, or other signal conditioning operations. In some examples, patient physiologic signals may be sensed and stored in a storage device, such as an electronic medical record system, and retrieved for use according to the method 500.

When the method 500 is used for detecting AT, the physiologic information received from the patient may include, among other information, ventricular contractions or ventricular beats detected and analyzed using, for example, the ventricular beat analyzer circuit 220, as discussed above with reference to FIG. 2. In an example, ventricular rate stability (VRS) may be determined using the detected ventricular beats, such as using a relative difference in ventricular cycle length between cardiac cycles measured from the cardiac signal. The VRS may alternatively be computed using variance, standard deviation, a metric derived from a histogram or a statistical distribution of ventricular cycle length over multiple cardiac cycles, or other variability measures or second-order statistics known in the art. In an example, the VRS may be recursively determined and updated on a beat-by-beat basis each time when a ventricular beat is detected.

Arrhythmia detection can include detecting respective arrhythmia indications (e.g., AT indications) in a plurality of distinct time windows, using segments of the received physiologic signal corresponding to the distinct time windows. In an example, the time windows may have the same duration T, such as approximately 2-5 minutes. In an example, the time windows are consecutive without overlapping to each other. Detection of arrhythmia indications in the respective distinct time windows may be performed using the arrhythmia detector circuit 230. In an example, AT indications may be detected based on ventricular rate variability within the signal segments defined by the time windows. In another example, AT indications may be detected based on signal morphology of ventricular beats within the time windows. In some examples, detection of AT indication may involve one or more statistical measures of ventricular rate or ventricular cycle length, such as a ventricular rate pattern, ventricular rate cluster, or Wenckebach score, as discussed above with reference to FIG. 3.

Arrhythmia detection can include detecting an arrhythmia onset representing the beginning of an episode, and detecting an arrhythmia termination representing the end of the detected episode. At 520, an arrhythmia onset (e.g., an AT onset) can be detected, such as using the onset detector 232. In an example of detecting AT, AT onset detection may be triggered in response to ventricular beats satisfying a specific condition. In an example, the AT detection may be triggered when the VRS satisfies an instability criterion. In another example, the AT detection may be triggered by physiologic features other than the VRS, such as a ventricular rate, a ventricular activation pattern, a ventricular signal morphology, or a cardiac event between consecutive ventricular beats.

An arrhythmia onset can be detected when the physiologic information during a first time period satisfies an onset condition. The first time period can be a time window $W_0$ having a duration T, as the example illustrated in FIG. 4. The onset condition can include an initial criterion (IC) and a confirmation criterion (CC), as discussed above with reference to FIG. 3. An arrhythmia onset can be detected when the physiologic information in the time window $W_0$ satisfies both the initial detection criterion (IC) and the confirmation criterion (CC). In an example, different physiologic information may be used for initial detection and confirmation. In an example, a first signal metric generated from the physiologic information in the time window $W_0$ is used for initial detection, while a second signal metric, also generated from the physiologic information in the time window $W_0$ but different than the first signal metric, is used for confirmation. The first signal metric can include atrial rate or heart (ventricular) rate variability determined from the physiologic information in the time window, and the initial detection criterion can be the atrial rate or the heart rate variability exceeding respective threshold values. The second signal metric can include physiological signal morphology features, or a heart rate pattern or organizational feature based on statistics of ventricular rate or ventricular cycle length, such as a "double decrement" ventricular rate pattern, a ventricular rate cluster, a Wenckebach score, as described above.

At 530, in response to the detected arrhythmia onset, an arrhythmia termination (e.g., AT termination) can be detected, such as using the termination detector 234. The arrhythmia termination can be detected when the physiologic information during a second time period, subsequent to and longer than the first time period, satisfies an exit condition different than the onset condition. In an example, the second time period can include two or more consecutive time windows subsequent to the first time window $W_0$. The consecutive time windows each have a duration substantially equal to the duration of the first time window used for detecting arrhythmia onset. The arrhythmia termination can be detected when respective physiologic information in each of the two or more consecutive time windows (e.g., consecutive windows $W_n$ and $W_{n+1}$) separately satisfy the exit condition. The exit condition can include an initial criterion and a confirmation criterion, as illustrated in FIG. 3, applied to each of the two or more consecutive time windows. In an example, an arrhythmia termination is detected when the respective physiologic information in at least one of the two or more consecutive windows (e.g., one of $W_n$ or $W_{n+1}$) fails the initial criterion (IC), or when the respective physiologic information in each of the second two or more consecutive windows (e.g., both $W_n$ and $W_{n+1}$) separately fails the confirmation criterion (CC).

Similar to the arrhythmia onset detection discussed above, different physiologic information may be used for initial detection and confirmation. In an example where arrhythmia termination is detected using two time windows $W_n$ or $W_{n+1}$, a first signal metric $X_n$ and a different second signal metric $Y_n$ can be generated from the physiologic information in time window $W_n$. The first signal metric $X_n$ is used for initial detection, and the second signal metric $Y_n$ is used for confirmation. Similarly, a first signal metric $X_{n+1}$ and a different second signal metric $Y_{n+1}$ can be generated from the physiologic information in time window $W_n$+1. The first signal metric $X_{n+1}$ is used for initial detection, and the second signal metric $Y_{n+1}$ is used for confirmation.

At 540, an arrhythmia episode can be determined based at least on a duration between the detected arrhythmia onset and the detected arrhythmia termination. In an example, an arrhythmia episode is detected as a sustained arrhythmia episode if the arrhythmia duration exceeds a duration threshold, or as a non-sustained arrhythmia episode if the arrhythmia duration is below the duration threshold. In some examples, arrhythmia characteristics can be generated from the detected arrhythmia episode. For example, from a detected AT episode, one or more AT characteristics can be generated, including, for example, AT duration, AT burden, among others.

The detected arrhythmia episode, and/or arrhythmia characteristics generated therefrom, may be provided to one or more processes 552, 554, or 556. At 552, the detected arrhythmia episode may be output to a user or a process, such as via an output device of the user interface unit 250. For example, an AT episode detected at 540 may be displayed on a display unit, including the sensed physiologic signal, VRS that triggered the AT detection, and other AT detection information (e.g., ventricular rate variability, morphology, or one or more statistical measures of ventricular rate or ventricular cycle length). Hard copies of the detection information may be generated. In various examples, alerts, alarms, emergency calls, or other forms of warnings may be generated to signal the system user about the detected arrhythmic episode.

At 554, a recommendation may be generated and provided to a user. The recommendation may include one or more of further diagnostic tests to be performed, anti-arrhythmic therapy to treat the detected arrhythmia or to alleviate the arrhythmic complications. The recommendation may include adjustment of one or more arrhythmia detection parameters, such as the instability criterion (e.g., threshold values) associated with AT onset detection and AT termination detection. At 556, a therapy may be delivered to the patient in response to the detected arrhythmia episode, such as via the optional therapy circuit 260 as illustrated in FIG. 2. Examples of the therapy may include electrostimulation therapy delivered to the heart, a nerve tissue, other target tissues, a cardioversion therapy, a defibrillation therapy, or drug therapy including delivering drug to a tissue or organ. In some examples, an existing therapy or treatment plan may be modified to treat the detected arrhythmia.

Figure 6:
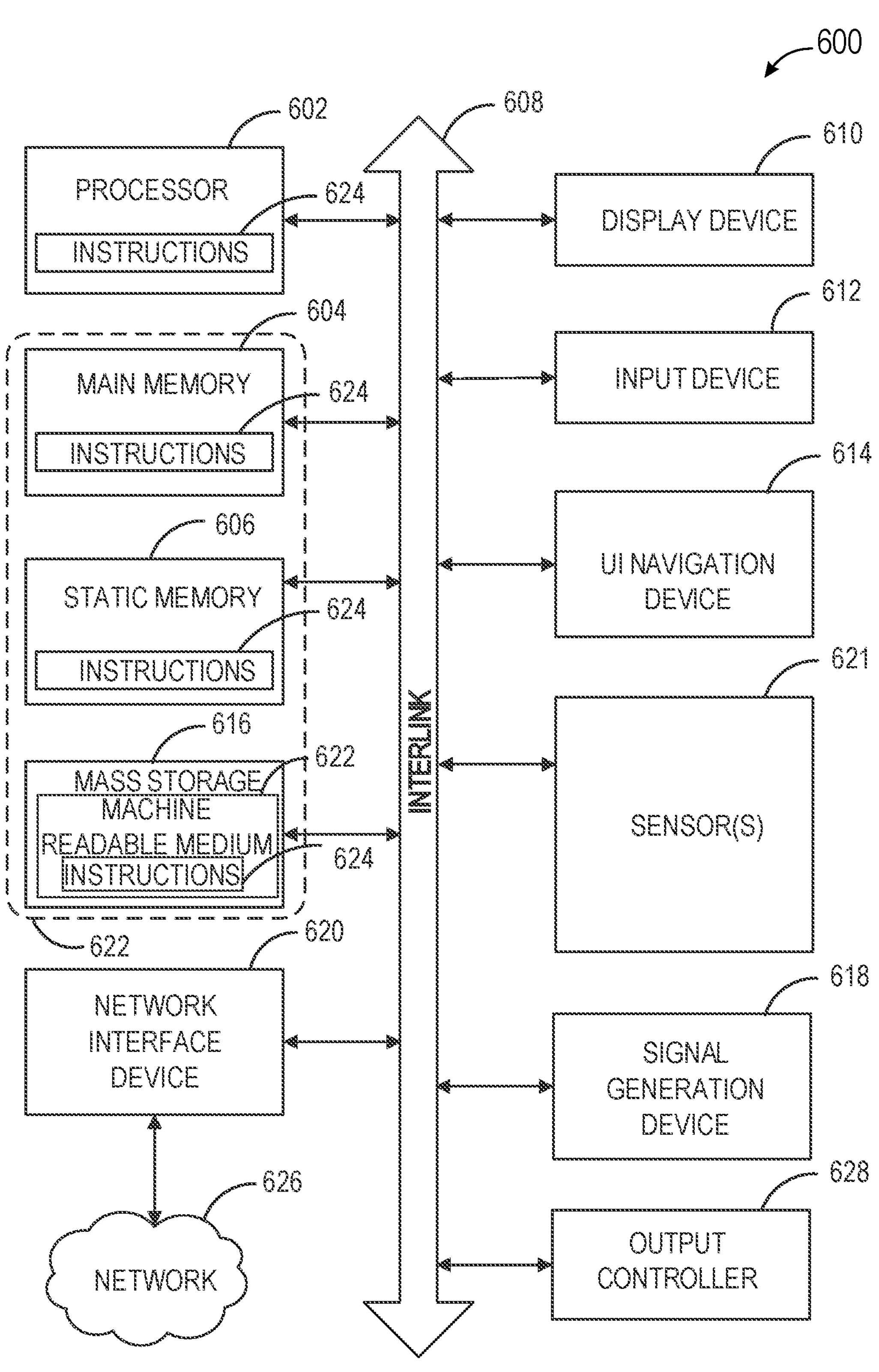
FIG. 6 illustrates generally a block diagram of an example machine upon which any one or more of the techniques (e.g., methodologies) discussed herein may perform.

FIG. 6 illustrates generally a block diagram of an example machine 600 upon which any one or more of the techniques (e.g., methodologies) discussed herein may perform. Portions of this description may apply to the computing framework of various portions of the LCP device, the IMD, or the external programmer.

In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610 (e.g., a raster display, vector display, holographic display, etc.), an alphanumeric input device 612 (e.g., a keyboard), and a user interface (UI) navigation device 614 (e.g., a mouse). In an example, the display unit 610, input device 612 and UI navigation device 614 may be a touch screen display. The machine 600 may additionally include a storage device (e.g., drive unit) 616, a signal generation device 618 (e.g., a speaker), a network interface device 620, and one or more sensors 621, such as a global positioning system (GPS) sensor, compass, accelerometer, or other sensors. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 616 may include a machine-readable medium 622 on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 may constitute machine-readable media.

While the machine-readable medium 622 is illustrated as a single medium, the term "machine-readable medium" may include a single medium or multiple media (e.g., a centralized or distributed database, and/or associated caches and servers) configured to store the one or more instructions 624.

The term "machine-readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine-readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 624 may further be transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802. 11 family of standards known as WiFi®, IEEE 802. 16 family of standards known as WiMax®), IEEE 802. 15. 4 family of standards, peer-to-peer (P2P) networks, among others. In an example, the network interface device 620 may include one or more physical jacks (e.g., Ethernet, coaxial, or phone jacks) or one or more antennas to connect to the communications network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system for improving arrhythmia detection in a patient, comprising:

a sensor circuit configured to sense physiologic information from the patient;

an arrhythmia detector circuit configured to:

receive user-programmed values of arrhythmia detection parameters including (i) a first time period and an associated onset condition for detecting an onset of an arrhythmia event, and (ii) a second time period subsequent to and longer than the first time period, and an associated exit condition different from the onset condition, for detecting a termination of the arrhythmia event, the different onset and exit conditions and time periods configured to improve arrhythmia detection;

receive the physiologic information from the sensor circuit, sensed from the patient over time, including during the first and the second time periods;

determine, based on the received physiologic information during the first time period, whether the onset condition is satisfied, and to detect the arrhythmia onset in response thereto;

in response to the detected arrhythmia onset, determine, based on the received physiologic information during the second time period, whether the exit condition is satisfied, and to detect the arrhythmia termination in response thereto; and detect an arrhythmia episode based on an arrhythmia duration between the detected arrhythmia onset and the detected arrhythmia termination; and an output unit configured to provide the detected arrhythmia episode to a user or a process.

2. The system of claim 1, wherein the first time period includes a first time window, and the second time period includes two consecutive time windows subsequent to the first time window, and wherein the arrhythmia detector circuit is configured to detect the arrhythmia termination when respective physiologic information in each of the two consecutive time windows of the second time period separately satisfy the exit condition.

3. The system of claim 2, wherein the two consecutive time windows each have a time duration substantially equal to a duration of the first time window.

4. The system of claim 2, wherein the onset condition includes an initial criterion and a confirmation criterion, and the arrhythmia detector circuit is configured to detect the arrhythmia onset when the received physiologic information in the first time window satisfies both the initial detection criterion and the confirmation criterion.

5. The system of claim 4, wherein the arrhythmia detector circuit is configured to:

generate a first signal metric and a different second signal metric from the received physiologic information in the first time window; and determine that the received physiologic information in the first time window satisfies the initial criterion using the first signal metric, and satisfies the confirmation criterion using the second signal metric.

6. The system of claim 5, wherein the arrhythmia episode includes atrial tachyarrhythmia, the first metric includes at least one of an atrial heart rate or a ventricular heart rate variability, and the second metric includes at least one of:

a ventricular rate cluster;

a Wenckebach score;

a double-decrement ratio; or a cardiac signal morphology.

7. The system of claim 2, wherein the exit condition includes an initial criterion and a confirmation criterion for each of the two consecutive time windows, and wherein the arrhythmia detector circuit is configured to detect the arrhythmia termination (i) when the respective physiologic information in at least one of the two consecutive time windows fails the initial criterion, or (ii) when the respective physiologic information in each of the two consecutive time windows separately fail the confirmation criterion.

8. The system of claim 7, wherein the arrhythmia detector circuit is configured to:

generate a first signal metric and a different second signal metric from the respective physiologic information in each of the two consecutive time windows; and for each of the two consecutive time windows, determine that the respective physiologic information in the corresponding time window fails the initial criterion using the first signal metric, or fails the confirmation criterion using the second signal metric.

9. The system of claim 8, wherein the arrhythmia episode includes atrial tachyarrhythmia, the first metric includes at least one of an atrial heart rate or a ventricular heart rate variability, and the second metric includes at least one of:

a ventricular rate cluster;

a Wenckebach score;

a double-decrement ratio; or a cardiac signal morphology.

10. The system of claim 1, wherein the arrhythmia detector circuit is configured to detect the arrhythmia episode including a sustained arrhythmia episode if the arrhythmia duration exceeds a threshold, or a non-sustained arrhythmia episode if the arrhythmia duration is below the threshold.

11. The system of claim 1, comprising an implantable cardiac monitor that includes the arrhythmia detector circuit.

12. The system of claim 1, comprising a therapy unit configured to provide therapy to the patient in response to the detected arrhythmia episode.

13. A method for improving arrhythmia detection in a patient, the method comprising:

sensing physiologic information from the patient using a sensor circuit;

receiving user-programmed values of arrhythmia detection parameters including (i) a first time period and an associated onset condition for detecting an onset of an arrhythmia event, and (ii) a second time period subsequent to and longer than the first time period, and an associated exit condition different from the onset condition, for detecting a termination of the arrhythmia event;

receiving the physiologic information from the sensor circuit, sensed from the patient over time, including during the first and the second time periods;

via an arrhythmia detector circuit, determining, based on the received physiologic information during the first time period, whether the onset condition is satisfied, and detecting the arrhythmia onset in response thereto;

in response to the detected arrhythmia onset, via the arrhythmia detector circuit, determining, based on the received physiologic information during the second time period, whether the exit condition is satisfied, and detecting the arrhythmia termination in response thereto;

detecting an arrhythmia episode based on an arrhythmia duration between the detected arrhythmia onset and the detected arrhythmia termination; and providing the detected arrhythmia episode to a user or a process.

14. The method of claim 13, wherein the first time period includes a first time window, and the second time period includes two consecutive time windows subsequent to the first time window each having a time duration substantially equal to a duration of the first time window, and wherein detecting the arrhythmia termination occurs when respective physiologic information in each of the two consecutive time windows of the second time period separately satisfy the exit condition.

15. The method of claim 14, wherein the onset condition includes an initial criterion and a confirmation criterion, and wherein detecting the arrhythmia onset occurs when the received physiologic information in the first time window satisfies both the initial detection criterion and the confirmation criterion.

16. The method of claim 15, comprising:

generating a first signal metric and a different second signal metric from the received physiologic information in the first time window; and determining that the received physiologic information in the first time window satisfies the initial criterion using the first signal metric, and satisfies the confirmation criterion using the second signal metric.

17. The method of claim 14, wherein the exit condition includes an initial criterion and a confirmation criterion for each of the two consecutive time windows, and wherein detecting the arrhythmia termination occurs (i) when the respective physiologic information in at least one of the two consecutive time windows fails the initial criterion, or (ii) when the respective physiologic information in each of the two consecutive time windows fails the confirmation criterion, wherein the method includes:

generating a first signal metric and a different second signal metric from the respective physiologic information in each of the two consecutive time windows; and for each of the two consecutive time windows, determining that the respective physiologic information in the corresponding time window fails the initial criterion using the first signal metric, or fails the confirmation criterion using the second signal metric.

18. The method of claim 13, wherein detecting the arrhythmia episode includes detecting a sustained episode if the arrhythmia duration exceeds a threshold, and detecting a non-sustained episode if the arrhythmia duration is below the threshold.

19. The method of claim 13, comprising delivering a therapy to the patient in response to the detected arrhythmia episode.

20. A system for improving arrhythmia detection in a patient, the system comprising:

an implantable or ambulatory medical device for detecting cardiac arrhythmia in a patient, the device comprising:

a sensor circuit configured to sense physiologic information from the patient;

an arrhythmia detector circuit of the implantable or ambulatory medical device, the arrhythmia detector circuit configured to:

receive user-programmed values of arrhythmia detection parameters including (i) a first time period and an associated onset condition for detecting an onset of an arrhythmia event, and (ii) a second time period subsequent to and longer than the first time period, and an associated exit condition different from the onset condition, for detecting a termination of the arrhythmia event, the different onset and exit conditions and time periods stored in a memory of the implantable or ambulatory medical device and configured to improve arrhythmia detection or implantable or ambulatory medical device performance;

receive the physiologic information from the sensor circuit, sensed from the patient over time, including during the first and the second time periods;

determine, based on the received physiologic information during the first time period, whether the onset condition is satisfied, and to detect the arrhythmia onset in response thereto;

in response to the detected arrhythmia onset, determine, based on the received physiologic information during the second time period, whether the exit condition is satisfied, and to detect the arrhythmia termination in response thereto; and detect an arrhythmia episode based on an arrhythmia duration between the detected arrhythmia onset and the detected arrhythmia termination.

* * * * *